(12) United States Patent
Jikuhara et al.

(10) Patent No.: US 7,048,540 B2
(45) Date of Patent: May 23, 2006

(54) AIR-DRIVEN CUTTING DEVICE FOR MEDICAL TREATMENT

(75) Inventors: Hirofumi Jikuhara, Kyoto (JP); Shozo Nakayama, Kyoto (JP); Noriyuki Tanaka, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 197 days.

(21) Appl. No.: 10/434,908

(22) Filed: May 9, 2003

(65) Prior Publication Data
US 2004/0005528 A1  Jan. 8, 2004

(30) Foreign Application Priority Data
May 10, 2002  (JP) .............................. 2002-135784

(51) Int. Cl.
*A61C 1/05* (2006.01)
(52) U.S. Cl. ........................................ 433/132; 415/904
(58) Field of Classification Search ................ 433/132, 433/115–116; 415/904
See application file for complete search history.

(56) References Cited

U.S. PATENT DOCUMENTS

| 3,218,028 | A | * | 11/1965 | Borden ........................ 415/201 |
| 3,324,552 | A | * | 6/1967 | Saffir ............................ 433/82 |
| 3,906,635 | A | * | 9/1975 | Lares et al. .................. 433/132 |
| 4,369,034 | A | * | 1/1983 | Garnier et al. ............... 433/115 |
| 5,823,774 | A | * | 10/1998 | Abbott et al. ................ 433/115 |
| 6,099,308 | A | * | 8/2000 | Nakanishi .................... 433/115 |

* cited by examiner

*Primary Examiner*—John J Wilson
(74) *Attorney, Agent, or Firm*—Koda & Androlia

(57) ABSTRACT

A air-driven cutting device for medical treatment (a handpiece (10)) comprises a housing (18) for a head portion (14). The housing (18) accommodates a rotary cylinder (60) for holding a cylindrical cutting tool (46) inserted through the tool inlet (42) of the housing, and a turbine blade (62) mounted around and secured on the rotary cylinder. With this arrangement, a compressed air is blown onto the turbine blade to rotate the turbine blade, the rotor and the cutting tool. Particularly, a part or a whole of the end portion of the rotary cylinder in the vicinity of the tool inlet is covered with the cover section (42) of the housing. Therefore, the rotary cylinder does not contact the teeth or the tissues of the buccal cavity.

5 Claims, 7 Drawing Sheets

AIR-DRIVEN CUTTING DEVICE FOR MEDICAL TREATMENT

RELATED APPLICATION

The present application claims the right of priority under 35 U.S.C. §119 of Japanese Patent Application No. 2002-135784, filed on May 10, 2002.

FIELD OF THE INVENTION

The present invention relates to an air-driven cutting device for a medical treatment such as dental treatment.

BACKGROUND OF THE INVENTION

FIG. 4 shows a part of an air-driven cutting device or handpiece for dental treatment, generally indicated by reference numeral (100). The handpiece (100) has a shaft section (102) and a head portion (104) which is formed integrally with the distal end of the shaft section (102). In the head portion (104), a housing (106) accommodates a rotor (110) for removably holding one end of a cylindrical cutting tool (108), bearings (112, 114) for rotatably supporting the rotor (110) and a turbine blade (116) mounted around the rotor (110) so that the turbine blade (116), the rotor (110) and the cutting tool (108) held by the rotor (110) are rotated by applying a compressed air from an air-supply passage (118) in the shaft (102), onto the turbine blade (116).

In this handpiece (100), an exhaust passage (not shown) is generally formed in the shaft section (102), and the air which has been applied onto the turbine blade (116) is exhausted through the exhaust passage. However, a part of the compressed air, after applying against the turbine blade (116), passes through the bearing (114) and a space (120) between the housing (106) and the rotor (110), and then, is injected at a high speed onto the distal end portion of the cutting tool (108) along the cutting tool (108). Further, the head portion (104) of the handpiece (100) has a mechanism for injecting cooling water to remove heat generated by the frictional contact between the rotating tool (108) and the tooth (122). This results in that the compressed air injected toward the distal end of the cutting tool (108) blows off the cooling water, so that a sufficient cooling effect can not be achieved.

SUMMARY OF THE INVENTION

To overcome the above problem, the present invention provides a air-driven cutting device for medical treatment comprising a housing for a head portion which accommodates a rotary cylinder for holding a cylindrical cutting tool inserted through the tool inlet of the housing, and a turbine blade mounted around and secured on the rotary cylinder. With this arrangement, a compressed air is blown onto the turbine blade to rotate the turbine blade, the rotary cylinder and the cutting tool. The feature of this instrument rests in that a part or a whole of the end portion of the rotary cylinder in the vicinity of the tool inlet is covered with the cover section of the housing.

In this air-driven cutting device for medical treatment, the housing is composed of an outer housing and an inner housing which is removably accommodated in the outer housing. The outer housing has an opening portion surrounding the above tool inlet, and the inner housing has an annular portion which is fitted in the above opening portion, and which is provided with the above cover section.

In another embodiment of the present invention, the housing for the head portion accommodates a rotary cylinder for holding a cylindrical cutting tool inserted through the tool inlet of the housing, and a turbine blade mounted around and secured on the rotary cylinder. With this arrangement, a compressed air is blown onto the turbine blade to rotate the turbine blade, the rotary cylinder and the cutting tool. The feature of the instrument rests in that the housing has, in the vicinity of the tool inlet, an air-leading portion which leads the air flowing from the turbine blade toward the tool inlet, to the outside in the radial direction of the cutting tool.

In this air-driven cutting device for medical treatment, the air-leading portion is preferably a hole formed in the housing. The housing is composed of an outer housing and an inner housing removably accommodated in the outer housing. Preferably, the outer housing has an opening portion surrounding the above tool inlet, and the inner housing has an annular portion which is fitted in the above opening portion and which has the above hole formed therein. Further, it is preferable that the above hole is formed closer on the side of the distal end of the cutting tool, than the end portion of the above rotary cylinder in the vicinity of the tool inlet.

Furthermore, it is preferable that, in the air-leading portion, an air guide portion in the vicinity of the turbine blade is formed extending from the central axis of the rotary cylinder toward a more outer side, than an air guide portion located distant from the turbine blade. Further, it is preferable that at least the air-injecting port of the air-leading portion is inclined from the central axis of the rotary cylinder to the outside and toward the distal end of the cutting tool.

PREFERRED EMBODIMENTS OF THE INVENTION

Figure 1:
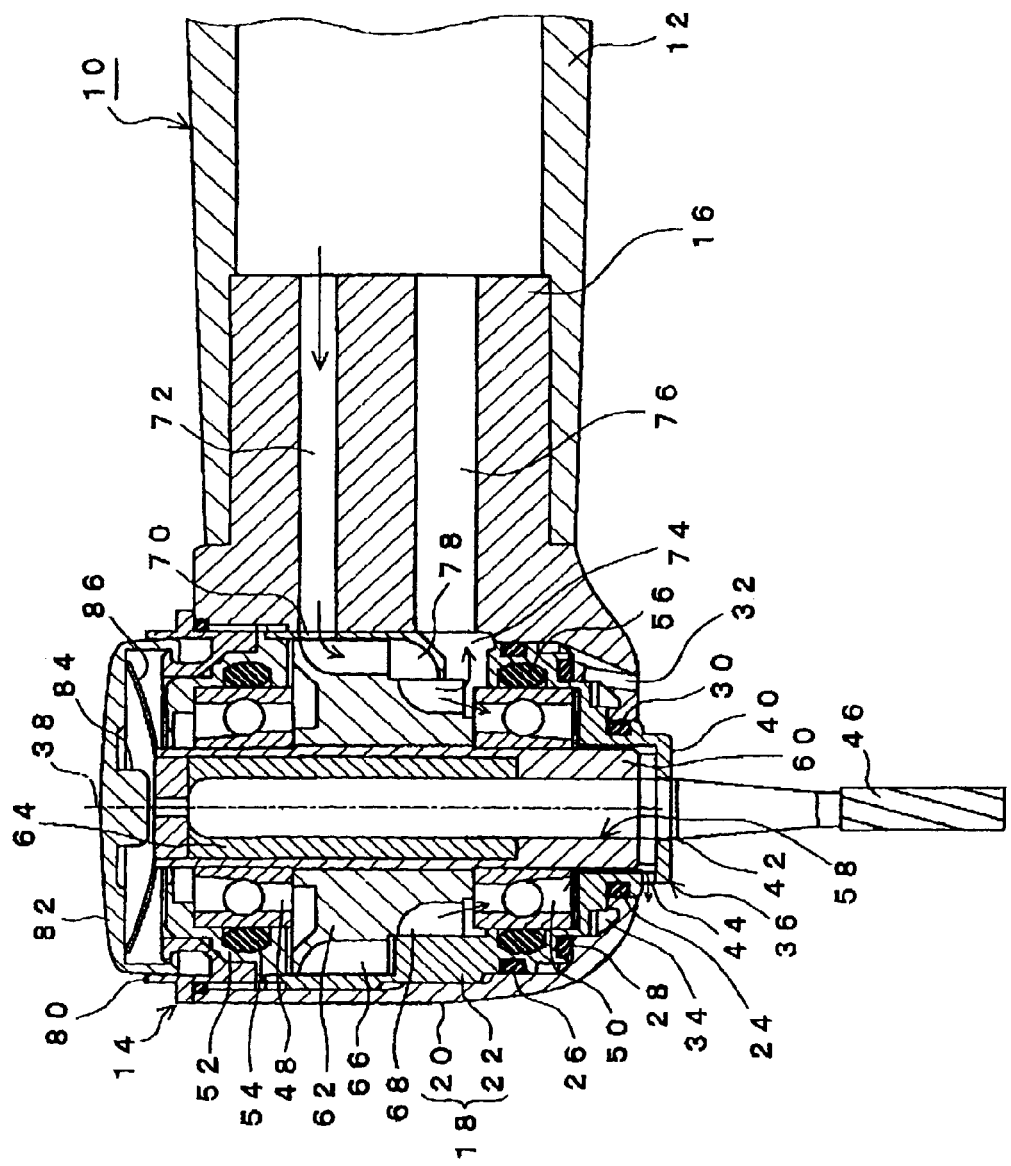
FIG. 1 is an enlarged sectional view of an essential part of a air-driven cutting device for medical treatment according to the present invention.

FIG. 1 is an enlarged sectional view of a part of a handpiece, generally indicated by reference numeral (10), which is a air-driven cutting device for medical or dental treatment according to the present invention. Generally, the handpiece (10) has a grip portion (12) to be held by an operator and a head portion (14) which is mounted on the distal end of the grip portion (12). As shown in FIG. 1, the grip portion (12) includes a cylindrical body having an opening defined at its distal end, e.g., the end portion on the left side on the drawing. The head portion (14), on the other hand, substantially has a shaft section (16) fitted in and secured to the opening of the distal end portion of the cylindrical body and a housing (18) for accommodating a cutting mechanism which will be described below.

The housing (18) has a cup-shaped outer housing (20) formed integrally with the shaft section (16), and a cup-shaped inner housing (22) which is removably fitted in the interior of the outer housing (20). The outer housing (20) has an upper opening and a lower opening. The upper opening is so sized that it allows the inner housing (22) to enter therethrough and fit in the interior of the outer housing (20). The lower opening (24), on the other hand, is so sized that it allows a part of the inner housing (22) to project downward therethrough.

Figure 2:
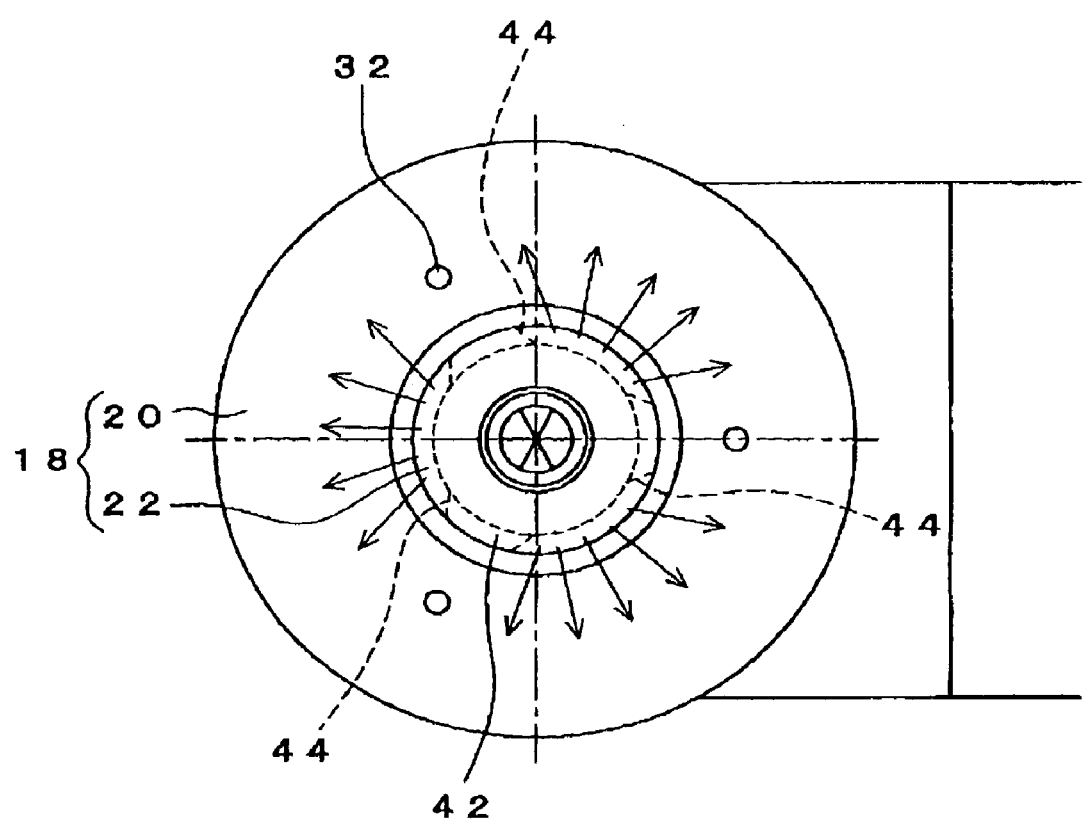
FIG. 2 is a bottom view of the air-driven cutting device for medical treatment shown in FIG. 1.

An outer configuration of the inner housing (22) corresponds to an inner configuration of the outer housing (20) so that, when the inner housing (22) is fitted in the outer housing (20), a possible gap defined between the inner housing (22) and the outer housing (20) can be minimized. A plurality of annular grooves are formed in the outer surface of the inner housing (22), confronting the inner surface of the outer housing (20). Sealing members such as O-rings 26, 28 and 30 are received in the annular grooves to seal between the outer housing (20) and the inner housing (22). As shown in FIGS. 1 and 2, a plurality of water-injecting holes (32) are formed at regular intervals in the base portion of the outer housing (20). The water-injecting holes (32) are connected to one another through an annular water passage (34) formed in the inner surface of the outer housing (20) confronting the inner housing (22). The holes (32) are also connected to a water-feeding passage (not shown) formed in the shaft section (16).

The inner housing (22) has an integrally formed annular portion (36) which projects downward through the lower opening (24) of the outer housing (20). The annular portion (36) is provided with a cover section (40) having an annular flange extending inwardly toward the central axis (38) of the housing (18). The cover section (40) has an opening (42) for the insertion of the cutting tool. A plurality of air-exhausting holes (44) each extending radially and outwardly are formed in the annular portion (36). In this embodiment, three holes are provided, however; the number of the holes is not restrictive to the present invention. The sectional area of each air-exhausting hole (44) is determined to be larger than the sectional area of the space defined between the cover section (40) and a cutting tool (46) inserted into the opening (42) of the cover section (40).

An upper bearing (48) and a lower bearing (50) are arranged inside the inner housing (22). The upper bearing (48) is held by an annular top housing (52) fixed in the upper opening of the inner housing (22), and the lower bearing (50) is held by the inner housing (22). As shown in FIG. 1, it is preferable to provide suitable sealing members such as O-rings (54, 56) between the upper bearing (48) and the top housing (52) and between the lower bearing (50) and the inner housing (22), respectively, so as to provide seals therebetween.

The upper bearing (48) and the lower bearing (50) rotatably support the rotary cylinder (60) of the rotor (58) which is disposed coaxially with the central axis (38) of the housing (18). An annular turbine blade (62), i.e., turbine, is fixedly mounted on the rotary cylinder (60) between the upper bearing (48) and the lower bearing (50) so that the rotary cylinder (60) rotates together with the turbine blade (62). The rotary cylinder (60) has a chuck (64), i.e., a cutting tool-holding mechanism, for holding a cylindrical cutting tool (46) which is inserted through the opening (42) defined in the cover section (40) of the inner housing (22).

In this embodiment, the turbine blade (62) has an upper blade portion (66) and a lower blade portion (68). Although the structure of the turbine blade (62) is not described in detail in this text, a double-blade turbine as disclosed in JP-A-2001-162416 can be used. On the other hand, air-supply passages (70, 72) are formed in portions of the inner housing (22) and the shaft section (16), confronting to the upper blade portion (66), respectively. Also, air-exhausting passages (74, 76) are formed in portions of the inner housing (22) and the shaft section (16), confronting to the lower blade portion (68), respectively. Further, air passage (78) or passages connecting the upper blade portion (66) to the lower blade portion (68) through a fluid is formed in the interior of the inner housing (22).

An annular locking ring (80) for locking the top housing (52) is fixed on the upper opening of the outer housing (20). The locking ring (80) holds the cap (82) so that the cap can move up and down. The cap (82) serving as an unlocking actuator (84) is usually held at a position shown in FIG. 1 by a spring (86) arranged inside the cap (82). When the cap (82) is pushed down against a spring (86), the unlocking actuator (84) unlocks the chuck (64) to allow the cutting tool (46) to be removed.

With the arrangement of the handpiece (10), the water fed through a water-feed tube (not shown) accommodated in the grip portion (12) is injected from the plurality of the water-injecting holes (32) toward the distal end of the cutting tool (46), through the water-feed passage of the shaft section (16) and the annular water passage (34) of the housing (18). On the other hand, the compressed air fed through an air-supply tube (not shown) accommodated in the grip portion (12) is blown onto the upper blade portion (66) of the turbine blade (62) through the air-supply passages (72, 70) of the shaft section (16) and the inner housing (22). The compressed air blown onto the upper blade portion (66) is then blown onto the lower blade portion (68) through the air passage (78). As a result, the turbine blade (62) is rotated and simultaneously, the rotor (58) having the turbine blade (62) mounted thereon is also rotated, and further, the cutting tool (46) held by the rotor (58) is rotated in combination.

Most of the compressed air blown onto the upper blade portion (66) and the lower blade portion (68) is discharged to the atmosphere from an exhaust hole (not shown) in the grip portion (12) through the exhaust passages (74, 76) in the inner housing (22) and the shaft section (16) and the internal space of the grip portion (12) which communicates with the exhaust passage. A part of the compressed air blown onto the lower blade portion (68) passes through the gap of the lower bearing (50) and the gap between the inner housing (22) and the rotor (58), further passes through the lower end face of the rotor (58), and finally is discharged from the air-exhausting hole (44) in a direction orthogonal to the central axis (38).

Here, air-exhausting holes are located closer to the side of the distal end of the cutting tool than the end portion of the rotary cylinder in the vicinity of the tool inlet.

Accordingly, the compressed air is not projected onto the distal end of the cutting tool (46), preventing the compressed air from entering between the cutting tool (46) and the teeth being cut with the cutting tool (46) to blow off the cooling water. The sectional area of the air-exhausting hole (44) is so designed to be larger than the sectional area of the space between the cover section (40) and the cutting tool (46), so that the noises caused by the compressed air discharged through the air-exhausting hole (44) is reduced considerably. Thus, an operator and a patient are not felt uncomfortable by such noises.

Further, the lower end portion of the rotor (58) is covered with the cover section (40) formed integrally with the inner housing (22) so that it does not contact the teeth being treated and the muscous membrane in the buccal cavity. This prevents the lower end portion of the rotor (58) from providing any damage to the teeth and the muscous membrane in the buccal cavity, or the rotor (58) from making any harmful contact with the teeth. Furthermore, in this embodiment, the housing (8) is composed of the outer housing (20) and the inner housing (22) and also the cover section (40) formed integrally with the inner housing (22) covers the lower end portion of the rotor (58), which allows the inner housing (22) to be replaced alone without the need of replacing the outer housing (20) when the inner housing (23) is damaged due to the contact with the teeth.

Figure 3:
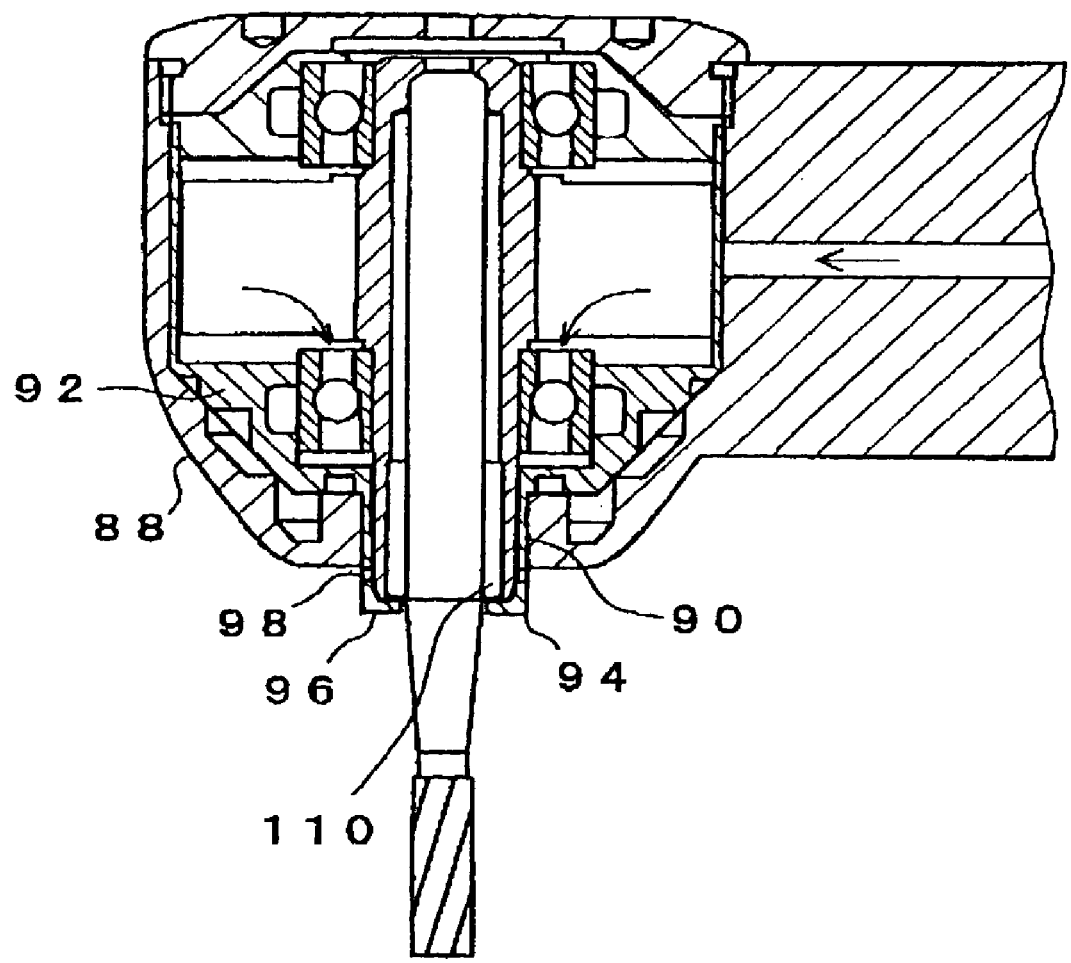
FIG. 3 is an enlarged sectional view of a part of another embodiment of the present invention which is obtained by adapting a conventional air-driven cutting device for medical treatment shown in FIG. 4, in accordance with the present invention.
Figure 4:
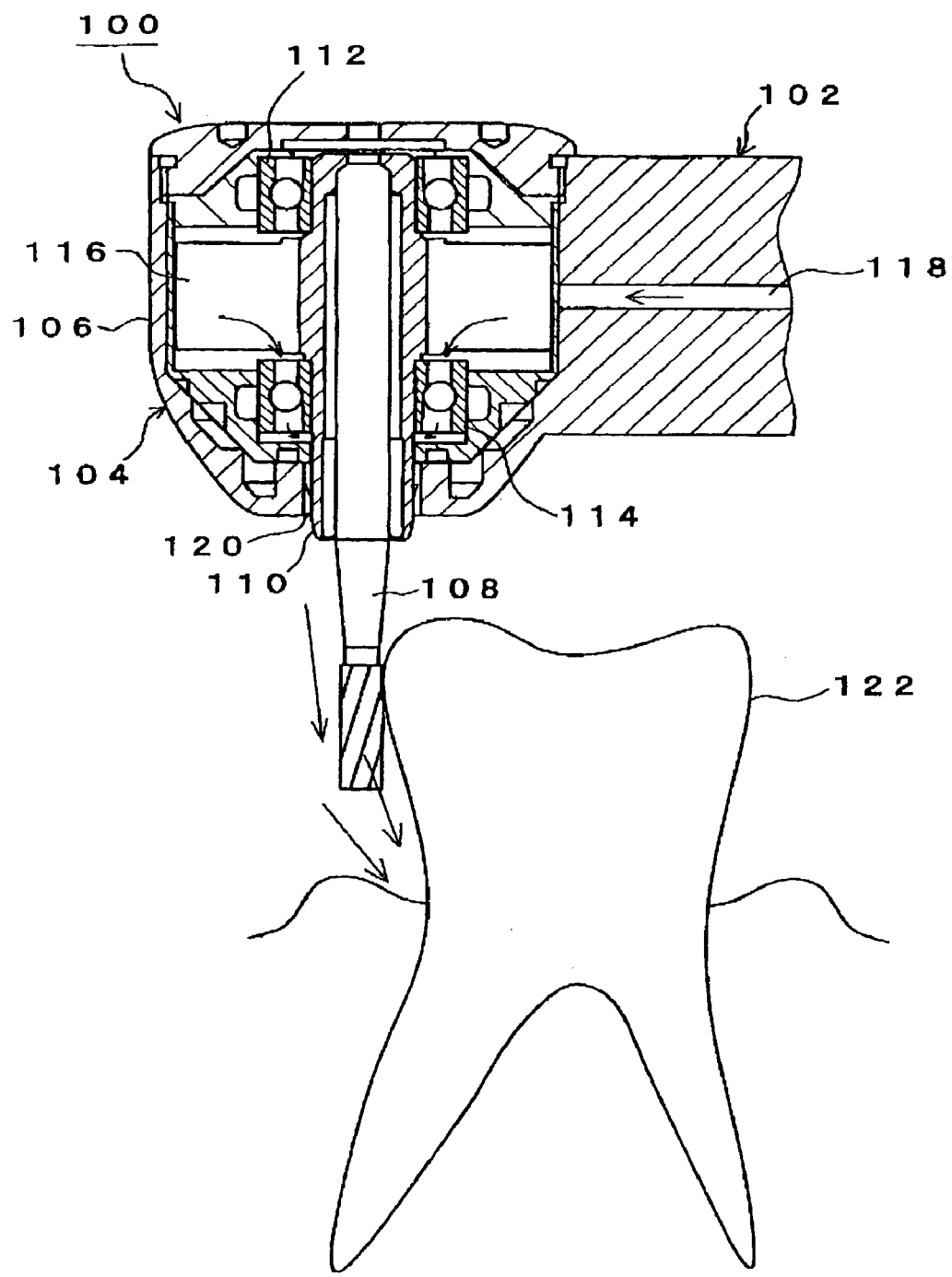
FIG. 4 is a sectional view of a conventional air-driven cutting device for medical treatment.

As can be seen from above, the cutting device of the present invention can be obtained by modifying the existing device. For example, as shown in FIG. 3, the conventional handpiece shown in FIG. 4 can be modified so that a part of the inner housing (92) is projected downward through the lower opening (90) of the outer housing (88). Also, a cover section (96) for covering the lower end portion of the rotor (110) is formed integrally with the projected annular portion (94). Further, at least one air-exhausting hole (98) is formed in this cover section (96) so as to lead the compressed air injected through the bearing, from the central axis toward the outside.

Figure 5:
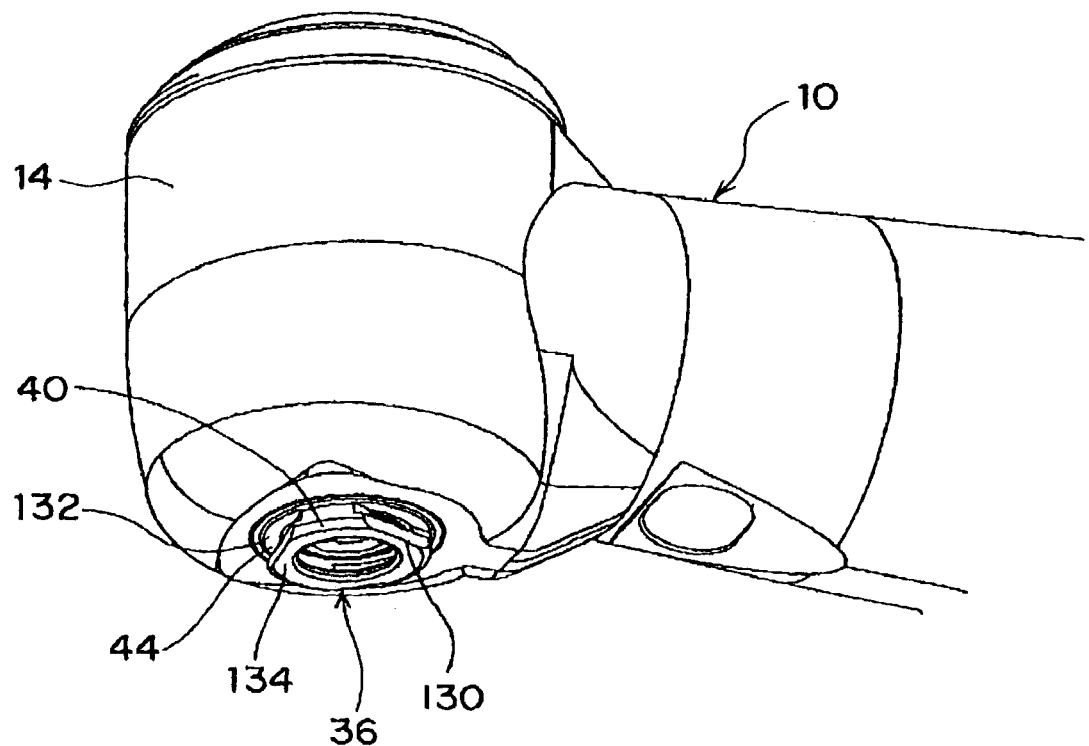
FIG. 5 is an enlarged perspective view of a air-driven cutting device for medical treatment according to a further embodiment of the present invention.
Figure 6:
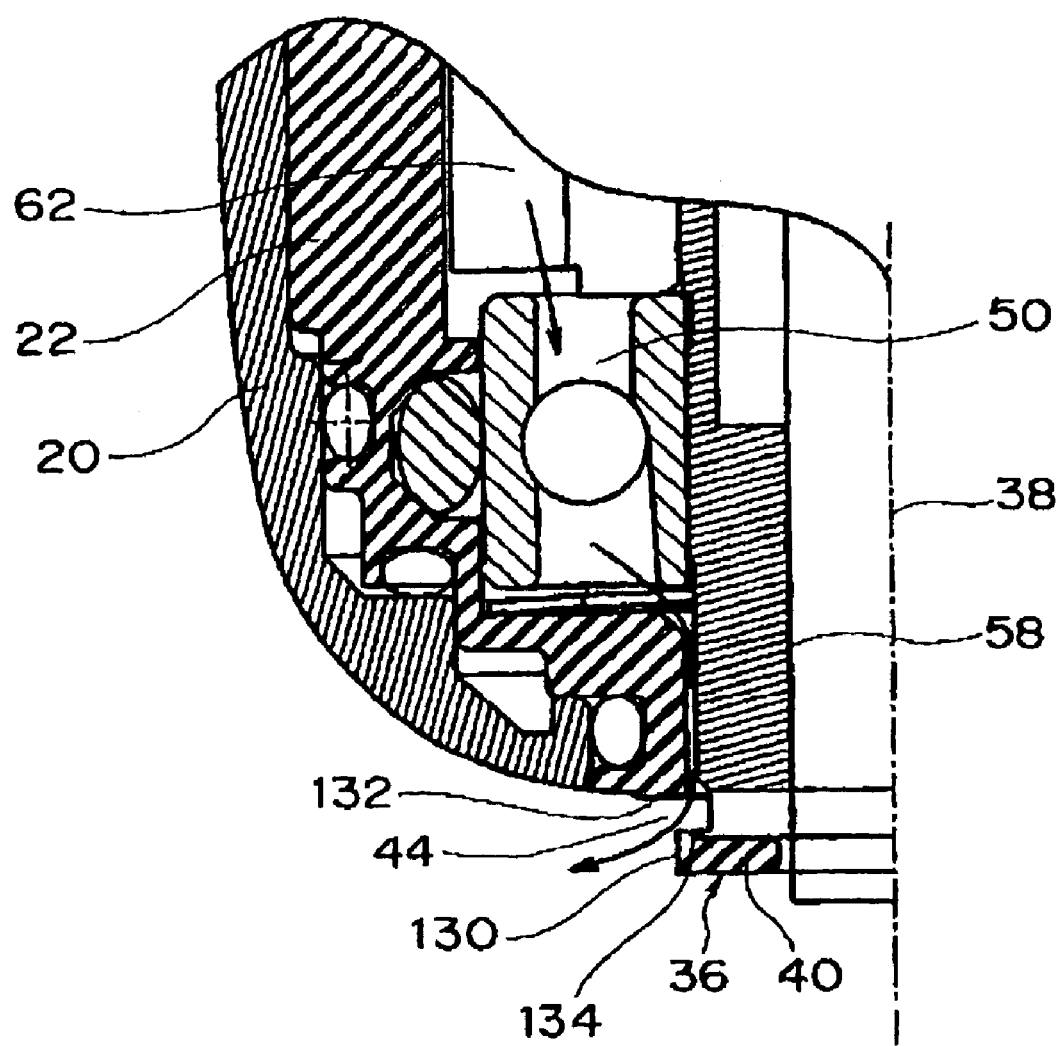
FIG. 6 is an enlarged sectional view of the air-driven cutting device for medical treatment shown in FIG. 5.
Figure 7:
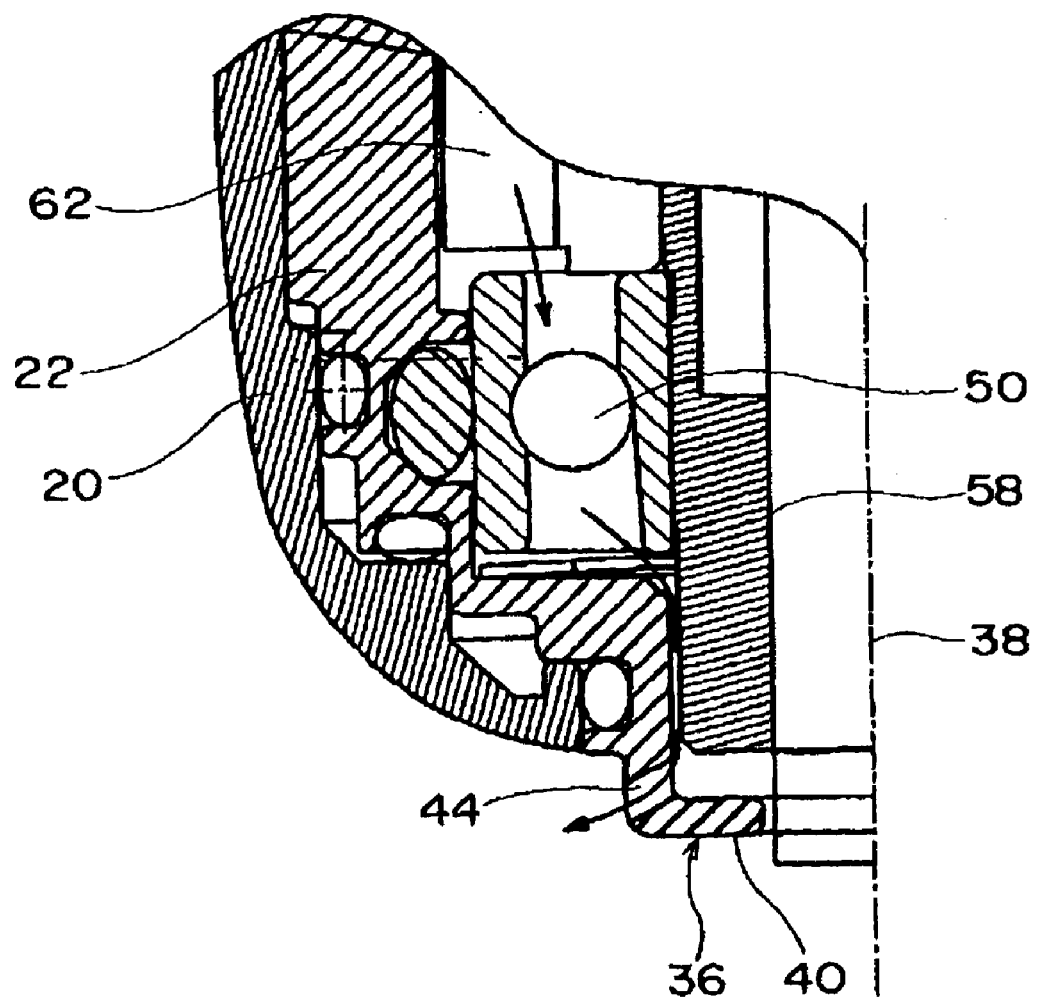
FIG. 7 is an enlarged sectional view of a air-driven cutting device for medical treatment according to a furthermore embodiment of the present invention.

It should be noted that various problems may arise when water droplets adhere to the head portion. For example, the water droplets on the head portion hinders the visual field of the operator. In another case, if the water droplets on the head portion then drop onto a resin used for a resin filler treatment by making use of photo-polymerization which requires a dried atmosphere, the treating effect is impaired. Further, the patient feels uncomfortable when such water droplets fall onto the patient. To overcome such problems, as shown in FIGS. 5 and 6, a cutout (130) (see FIG. 5) is formed on a portion which is a part of the annular cover (40) forming the air-exhausting outlet (44) as an air-leading portion, and the air-guiding portion (132) in the vicinity of the turbine blade (62) is formed extending toward a more outer side from the central axis (38) than the air-guiding portion (134) located distant from the turbine blade, so that the air injected from the air-exhausting outlet (44) is caused to outflow obliquely toward the distal end of the cutting tool. Furthermore, as shown in FIG. 7, a similar effect can be obtained by forming the air-exhausting outlet (44) extending from the central axis (38) toward outside, and slightly inclining toward the distal end of the cutting tool. In this regard, the region within which the air-exhausting outlet (44) is obliquely formed includes at least the vicinity of the injecting port of the air-exhausting outlet (44).

As is understood from the foregoing description, according to the present invention, a part or a whole of the end portion of the rotary cylinder in the vicinity of the opening for the insertion of the tool is covered with the cover section of the housing. Therefore, the end portion of the rotary cylinder does not touch the teeth or the muscous membrane of the buccal cavity of a patient to injure the same, nor is damaged by contact with the teeth.

Furthermore, according to the present invention, the housing has, in the vicinity of the tool inlet, the air-guide portion which guides the air flowing from the turbine blade toward the tool inlet, to the outside in the radial direction of the cutting tool. Therefore, the compressed air led by this air-leading portion does not blow off cooling water, so that the cooling effect is not impaired.

What is claimed is:

1. An air-driven cutting device for medical treatment, comprising:
    a housing for a head portion which accommodates a rotary cylinder for holding a cylindrical cutting tool inserted through a tool inlet of the housing and a turbine blade mounted around and secured on the rotary cylinder, wherein:
    a compressed air is blown onto the turbine blade to rotate the turbine blade, the rotary cylinder and the cutting tool,
    a part or a whole of the end portion of the rotary cylinder in the vicinity of the tool inlet is covered with a cover section of the housing:
    said cover section includes an opening through which said tool projects;
    said cover closes said housing such that compressed air is prevented from escaping from said housing and being injected at a high speed onto a distal end of said tool;
    the housing is composed of an outer housing and an inner housing removably accommodated in the outer housing, said inner housing having the tool inlet, said outer housing having an opening portion surrounding the tool inlet, and said inner housing having an annular portion which is fitted in said opening portion and which is provided with said cover section; and
    at least one radially extending hole formed in said housing for leading air flowing from the turbine blade to an outside of said housing;
    whereby cooling water on said distal end of said tool is not blown off.

2. An air-driven cutting device for medical treatment, comprising:
    a housing for a head portion which accommodates a rotary cylinder for holding a cylindrical cutting tool inserted through a tool inlet of the housing, and a turbine blade mounted around and secured on the rotary cylinder,
    wherein a compressed air is blown onto the turbine blade to rotate the turbine blade, the rotary cylinder and the cutting tool,
    wherein the housing has, in the vicinity of the tool inlet, an air-leading portion which leads an air flowing from the turbine blade toward the tool inlet, to an outside of said housing in a radial direction of the cutting tool,
    the air-leading portion is at least one radially extending hole formed in the housing; and
    the housing has an outer housing and an inner housing removably accommodated in the outer housing, said inner housing having the tool inlet, said outer housing having an opening portion surrounding the tool inlet and said inner housing having an annular portion fitted in said opening portion and having said radially extending hole formed therein;
    whereby cooling water on a distal end of said tool is not blown off by said compressed air.

3. The device according to claim 2, wherein said radially extending hole is located on the side of the housing and not adjacent to the end portion of the rotary cylinder in the vicinity of the tool inlet.

4. The device according to any one of claims 2 and 3, wherein, in said air-leading portion, an air guide portion in the vicinity of the turbine blade is formed extending from the central axis of the rotary cylinder toward a more outer side than an air guide portion located distant from the turbine blade.

5. The device according to any one of claims 2 and 3, wherein at least said air-leading portion is inclined from the central axis of the rotary cylinder toward the outside and toward the distal end of the cutting tool.

* * * * *